United States Patent [19]

Kline

[11] 3,935,160

[45] Jan. 27, 1976

[54] DIALKYLAMINOMETHYLPHENOLS AS CATALYST DEACTIVATORS FOR STEREOREGULAR DIENE POLYMERS

[75] Inventor: Richard H. Kline, Cuyahoga Falls, Ohio

[73] Assignee: The Goodyear Tire & Rubber Company, Akron, Ohio

[22] Filed: Jan. 9, 1975

[21] Appl. No.: 539,666

Related U.S. Application Data

[63] Continuation-in-part of Ser. No. 356,693, May 2, 1973, abandoned.

[52] U.S. Cl. ............... 260/45.8 NT; 260/45.8 NZ; 260/45.9 R
[51] Int. Cl.² ............................................. C08J 3/20
[58] Field of Search. 260/45.9 R, 45.8 NZ, 45.8 NT

[56] References Cited
UNITED STATES PATENTS

| | | | |
|---|---|---|---|
| 2,962,531 | 11/1960 | Coffield | 260/45.9 R |
| 3,047,559 | 7/1962 | Mayor et al. | 260/94.3 |
| 3,115,466 | 12/1963 | Orloff et al. | 260/45.9 R |
| 3,560,432 | 2/1971 | Briggs et al. | 260/45.9 R |

*Primary Examiner*—V.P. Hoke
*Attorney, Agent, or Firm*—F. W. Brunner; J. A. Rozmajzl

[57] ABSTRACT

Dialkylaminomethylphenols such as 2,4,6-tris (dimethylaminomethyl) phenol are added, preferably along with another phenolic antioxidant prior to exposure to oxidative conditions, to a stereoregular polymer, a major portion of said polymer consisting of segmeric units derived from conjugated diolefin monomers, said polymer containing transition metal catalysts, to help prevent oxidative degradation of the polymer.

9 Claims, No Drawings

DIALKYLAMINOMETHYLPHENOLS AS CATALYST DEACTIVATORS FOR STEREOREGULAR DIENE POLYMERS

This application is a continuation-in-part of U.S. application Ser. No. 356,693 filed May 2, 1973, now abandoned.

This invention relates to catalyst deactivators for synthetic elastomers. More particularly, it relates to the addition of dialkylaminomethylphenols to stereoregular polymers prepared using transition metal containing catalysts.

Stereospecific polymerizations are well known in the art. They often are used to produce stereoregular polymers from systems containing conjugated diolefins such as 1,3-butadiene and isoprene, alone or with other comonomers. Organometallic catalysts of the Ziegler and Natta types are typical of the polymerization catalysts used. Some of these metallic catalysts, when they remain as residues in the finished polymer, cause severe stabilization problems, i.e., tend to accelerate the oxidative degradation of the polymer. Those skilled in the art are constantly searching for deactivators which will prevent these metallic catalyst residues from causing severe oxidative degradation and to do so without causing severe discoloration.

It is an object of the present invention to provide a new class of metallic catalyst deactivators. It is also an object of the present invention to provide a process for preventing the oxidative degradation of stereoregular polymers prepared using transition metal containing catalysts and containing a major amount of segmeric units derived from conjugated diolefinic monomers. Other objects will become apparent as the description proceeds.

These objects are accomplished by incorporating a dialkylaminomethylphenol into a stereoregular polymer prepared from a transition metal containing catalyst prior to exposure of the polymer to substantial oxidative degradation conditions.

These dialkylaminomethylphenols (DAAMP) have the following structural formula:

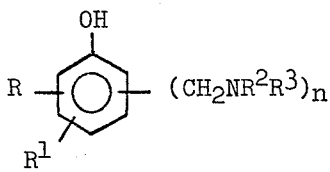

wherein $R^2$ and $R^3$ are selected from the group consisting of alkyl radicals having 1 to 4 carbon atoms (preferably methyl), hydroxy alkyl radicals having 2 to 4 carbon atoms (preferably 2), or wherein $R^2$ and $R^3$ can be joined through a member of the group consisting of —CH$_2$— and —O— to constitute with the attached nitrogen atom a heterocyclic radical (preferably piperidino or morpholino), wherein R and $R^1$ are selected from the group consisting of hydrogen and alkyl radicals having 1 to 8 carbon atoms and even alkyl radicals having 9 to 12 carbon atoms, wherein n is an integer from 1 to 3 and wherein the total number of substituents on the phenolic ring in addition to the hydroxy group is from 1 to 5 with the proviso that when the phenolic ring contains 4 or 5 substituents the radicals —(CH$_2$NR$^2$R$^3$)n are in ortho or para positions.

Preferably n is 2 or 3. Preferably the dialkylaminomethyl groups occupy at least one position ortho to the hydroxyl group, most preferably both ortho positions. The total number of substituents on the ring is preferably three.

This class of phenolic compounds is illustrated by the following list of compounds.

2,4,6-tris(dimethylaminomethyl) phenol
2,6-bis(dimethylaminomethyl)-p-cresol
2,4,6-tris(dimethylaminomethyl)-m-cresol
2,6-bis(dimethylaminomethyl)-4-tert.butylphenol
2,6-dipiperidinomethyl-p-cresol
2-piperidinomethyl-6-tert.butyl-p-cresol
2,6-dimorpholinomethyl-p-cresol
2,6-bis(dimethylaminomethyl)-4-(1,1,-dimethylbutyl)phenol
2,6-ditert.butyl-4-dimethylaminomethylphenol
2,4-bis(dimethylaminomethyl)-6-tert.butylphenol
2,6-bis(di n butylaminomethyl)-p-cresol
2,4,6-tris(diethylaminomethyl)-phenol
2,6-ditert.butyl-4-piperidinomethylphenol
2-dimethylaminomethyl-6-tert.butyl-p-cresol
2,4-bis(dimethylaminomethyl)-6-tert.butyl-m-cresol
2,4,6-tris[bis(2-hydroxyethyl)aminomethyl] phenol
2,6-bis[bis(2-hydroxyethyl)aminomethyl]-p-cresol
2,4,6-tris(dimethylaminomethyl)3,5-xylenol
2,6-bis(diethylaminomethyl)-4-tert.butylphenol
2,6-bis(dimethylaminomethyl)-4-isopropylphenol The phenolic deactivators can be prepared in the following general manner which is illustrative, but not limiting.

A solution of a phenol, a secondary amine and formaldehyde is heated under reflux for from 1 to 5 hours. The amine and formaldehyde are used in an amount ranging from 1 to 1.5 moles for each free ortho or para position per mole of phenol. Formaldehyde is most conveniently used in the form of formalin, a 37 percent aqueous solution. If the phenol and/or the amine are not water soluble, a water miscible solvent such as ethanol may be added in an amount sufficient to make the reaction mixture homogeneous. At the end of the heating period, the reaction mixture is allowed to cool and the product is separated by the most convenient method, e.g., filtration, distillation, extraction, etc.

Stereoregular polymers prepared from conjugated diolefinic monomers, with or without minor amounts of olefinic hydrocarbons, are commonly prepared at low pressures and at moderate temperatures employing transition metal containing catalysts such as those formed by the interaction of organometallic compounds, such as tralkylaluminum compounds and transition metal compounds such as titanium tetrahalides (e.g., see U.S. Pat. No. 3,047,559 and Belgian Pat. No. 551,851). The term "transition metal" refers to transition element. The transition elements are those elements which have partly filled d and f shells in their normal state or in any of their commonly occurring oxidation states. All of the transition elements are metals.

U.S. Pats. Nos. 3,170,907 and 3,471,462 describe methods involving the use of a nickel catalyst to prepare stereoregular polymers. U.S. Pat. No. 3,094,514 describes the preparation of stereoregular polymers using a cobalt catalyst system. Cerium catalysts also can be used, as described in Kautschuk und Gummi Kunststoffe, 29, 293(1969).

Stereoregular polymers are produced commercially in large quantities from monomers such as butadiene and isoprene, using transition metal containing catalysts to produce such representative polymers as exemplified by high cis-1,4,-polybutadiene and cis-1,4-polyisoprene. A stereoregular polymer normally contains a predominantly large portion of some particular structure such as greater than 85 percent cis-1,4-polybutadiene, or at least 90 percent cis-1,4-polyisoprene. Stereoregular polymers containing approximately equal amounts of two types of structure, such as alternating units of cis-1,4- and trans-1,4-polybutadiene or 1,2- and 3,4-polyisoprene may be prepared by certain transition metal containing complex catalysts [see Journal of Polymer Science, C, 22, 221, (1968) and Journal of Polymer Science, B, 6, 299 (1968)]. The transition metal catalyst residues may be chelated and deactivated by the addition of one or more of the dialkylaminomethyl phenols which are the subject of this invention.

Cis-1,4-polyisoprene rubber may conveniently be produced in accordance with the procedures described in the following references, although these procedures are not intended to be limiting.

1. "Synthetic Natural Rubbers from Isoprene" Rubber and Plastic Age Vol. 39 No. 11 Page 938 (1958) by Mayor, Saltman and Pierson
2. "Cis-1,4-Polyisoprene prepared with Alkyl Aluminum and Titanium Tetrachloride" Industrial and Engineering Chemistry, Vol. 50, Pages 1507–1510 (1958) by Adams, Stearns, Smith and Binder Cis-1,4-polybutadiene rubbers may conveniently be produced in accordance with the procedures described in the following references, although these procedures are not intended to be limiting.

1. "New Controlled-Structure Polymer of Butadiene" Rubber and Plastic Age, March 1961 Pages 276–282 by W. W. Crouch
2. "1,4-Cis-Polybutadiene" Gummi und Asbest Vol. 13, page 1026 (1960)

Not all stereoregular polymers will benefit by the practice of the present invention (e.g., polybutadiene prepared with a lithium catalyst). Only those containing the residue of a transition metal catalyst will benefit.

Preferably a hindered monohydric phenolic antioxidant or hindered bisphenolic antioxidant is added along with the DAAMP. Although all of the DAAMP compounds are metal deactivators, many are not very effective as antioxidants.

The phenolic stabilizers are well known as effective stabilizers for natural and conventional synthetic rubbers. Hindered phenolic antioxidants are those that have a bulky secondary or tertiary alkyl group attached to the phenolic ring in at least one of the positions ortho to the hydroxy group.

Illustrative phenolic antioxidants are shown in the du Pont bulletin entitled, "Antioxidants and Antiozonants" at pages 12–21. The level of phenolic antioxidant can vary, but normally is added in the amount of 0.1 to 10 parts by weight per 100 parts by weight of polymer. A preferred range is from 0.5 to 1.5 parts by weight. Typical of the hindered monohydric phenolic antioxidants are the 2,6-dialkylated para cresols, such as 2,6-ditert.butyl-p-cresol. Typical of the hindered bisphenolic antioxidants is 2,2'-methylene bis(4-methyl-6-tert.butyl phenol).

If either the phenolic antioxidant or DAAMP compound is omitted, the resistance of the resulting polymer to oxidative degradation will be lowered.

The DAAMP compound (or mixtures thereof) and the phenolic antioxidant (or mixtures thereof) should be added to the polymer solution (stereospecific polymerizations normally being carried out in an inert organic solvent such as hexane) preferably as soon as the polymerization reaction is completed and necessarily before the polymer solution is exposed to air or subjected to any heating or drying operations. The DAAMP and the phenolic compound may be added to the polymer solution in the form of a previously prepared mixture or they may be added to the polymer solution separately. A preferred method, from a performance point of view, for incorporating these materials into the synthetic polymers is to first introduce the metal deactivator to the dilute polymer cement and then after a brief time lag to introduce the antioxidant to the dilute polymer cement, both additions being accomplished before the polymer is subjected to any conditions that will cause it to deteriorate such as exposure to air, heating or drying.

The level of the DAAMP compound will vary depending upon the amount of catalyst used in preparing the polymer. The amount of DAAMP is normally from one mole to five moles per mole of transition metal in the catalyst.

The stabilized polymers may be used according to any of their standard uses, e.g., the high cis rubbery polybutadiene and polyisoprene polymers may be used in the manufacture of automobile tires.

The following examples are intended to illustrate but not to limit the practice of the present invention as well as to demonstrate the superiority of the DAAMP over related compounds. Unless indicated otherwise, all parts are parts by weight.

Examples 1 to 3 reveal the preparation of three representative compounds of the present invention.

EXAMPLE 1

2,4,6-tris(dimethylaminomethyl)phenol

A mixture of 94 grams of phenol, 450 grams of 40 percent dimethylamine solution and 270 grams of water is cooled to 25° C. and 284 grams of 37 percent formaldehyde solution is added in 20 minutes at 25°–30° C. The mixture is stirred for 1½ hours at 25°–30° C. and then heated at 90°–95° C. for 2 hours. One hundred eighty grams of sodium chloride are added and the mixture is stirred for 20 minutes. The layers are then separated. The organic (upper) layer is distilled under vacuum to a pot temperature of 150° C./20 mm. The pale yellow oily residue weighs 208 grams (82.2 percent yield).

EXAMPLE 2

2-piperidinomethyl-6-tert.butyl-p-cresol

A solution of 164 grams of 2-t.butyl-p-cresol in 200 ml. of ethanol is added at 25° C. to a solution containing 84 grams of 37 percent formaldehyde, 102 grams of piperidine and 300 ml. of ethanol. The mixture is heated at reflux for 5 hours and is then cooled to room temperature. The material which precipitates on cooling is filtered off and dried. The yield of white crystalline solid (m.p. 82°–84° C.) is 247 grams (94.5 percent of theory).

EXAMPLE 3

2,6-bis(dimethylaminomethyl)-4-t.butylphenol

A solution of 37.5 grams of p-t.butylphenol in 100 ml. of ethanol is added at room temperature to a mixture of 47 grams of 37 percent formalin and 70 grams of 40 percent dimethylamine solution. The mixture is heated at reflux for 3 hours, is then cooled and the layers are separated. The organic layer is distilled under vacuum to a pot temperature of 100° C./15 mm. The residue, which crystallizes on cooling to a white solid (m.p. 38°–40° C.), weighs 63 grams (95 percent of theory).

Isoprene was polymerized in 4-ounce bottles in pentane solution using a triisobutyl aluminum-titanium tetrachloride catalyst. To each freshly prepared solution of cis-1,4-polyisoprene (before exposure to air) were added one of the compounds of the present invention and one part of the antioxidant, 2,6-ditert.hexyl-p-cresol. Both deactivator and antioxidant were added in the form of benzene solutions with the deactivator being added first. Each benzene-pentane solution was mixed thoroughly and the solvents then evaporated to form a film. The amount of oxygen absorbed by the resulting films at 90° C. was measured. The results are listed in Table I.

Table I

| Compound | Hours to 1% Oxygen Absorbed at 90°C. |
|---|---|
| 2,4,6-tris(dimethylaminomethyl) phenol mixture of 2,6-bis(dimethylaminomethyl)-p-cresol and 2,4,6-tris(dimethyl-aminomethyl)-m-cresol | 420/0.3% |
| | 475/0.3% |
| 2-piperidinomethyl-6-tert-butyl-p-cresol | 695 |
| 2,6-bis(dimethylaminomethyl)-4-tert-butylphenol | 648 |
| 2,4,6-tris[bis(2-hydroxyethyl)amino-methyl] phenol | 420 |
| 2,6-ditert.butyl-4-piperidinomethyl phenol | 363 |
| 2,6-ditert.butyl-4-dimethylaminomethyl phenol | 350 |
| 2,4,6-trimorpholinomethylphenol | 272 |

No control without additive was run because such a sample contains so much gel that a satisfactory film can not be formed. 2-Dimethylaminomethyl-6-tert.butyl-p-cresol and 2,4-bis(dimethylaminomethyl)-6-tert.butylphenol also were tested in a manner similar to that above and acted as deactivators.

The present invention is not limited to the previously recited examples. Any of the deactivators previously described herein could be used in any previously recited working examples as well as the one recited below. Likewise, different polymers, as described herein, could be prepared using different catalysts described herein and effective deactivation would result.

2,6-Bis(dimethylaminomethyl)-4-tert.nonyl phenol was prepared by heating a mixture of 675 grams of formalin (37 percent aqueous formaldehyde), 1,050 grams of a 40 percent aqueous solution of dimethylamine, 825 grams of 4-tert.nonly phenol and 1,750 milliliters of ethanol at reflux for 7 hours. The mixture was allowed to cool and the layers were separated. Solvent was removed from the organic layer under vacuum leaving 1,233 grams of product.

The above compound was evaluated by adding it in the form of a benzene solution to samples of a cement of cis-1,4 polyisoprene. The concentration of phenolic antioxidant to cis-1,4 polyisoprene was one part by weight per 100 parts by weight of polyisoprene. 2,6-Ditert.butyl-pcresol was then added in the amount of one part per 100 parts by weight of polyisoprene. After mixing thoroughly, the cement was pured into aluminum trays and allowed to evaporate. The resulting film was tested in an oxygen absorption unit at 90° C. The sample absorbed 1 percent oxygen in 878 hours thus indicating that it was effectively stabilized.

While certain representative embodiments and details have been shown for the purpose of illustrating the invention, it will be apparent to those skilled in this art that various changes and modifications may be made therein without departing from the spirit or scope of the invention.

What is claimed is:

1. A process of preventing the oxidative degradation of elastomeric stereoregular polymers, a major portion of said polymer consisting of segmeric units derived from conjugated diolefinic monomers, said polymers containing transition metal catalyst residues, comprising adding a dialkylaminomethylphenol to the stereoregular polymer prior to exposure of the polymer to substantial oxidative degradation conditions, the dialkylaminomethylphenols having the following structural formula

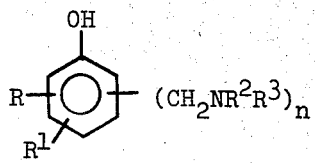

wherein R and R¹ are selected from the group consisting of hydrogen and alkyl radicals having 1 to 12 carbon atoms, wherein $n$ is an integer from 1 to 3, wherein, when $n$ is 1, $R^2$ and $R^3$ are joined through a member of the group consisting of —$CH_2$— and —O — to constitute with the attached nitrogen atom a heterocyclic radical and wherein, when $n$ is 2 or 3, $R^2$ and $R^3$ are selected from the group consisting of alkyl radicals having 1 to 4 carbon atoms, hydroxy alkyl radicals having 2 to 4 carbon atoms or can be joined through a member of the group consisting of —$CH_2$— and —O— to constitute with the attached nitrogen atom a heterocyclic radical and wherein the total number of substituents on the phenolic ring in addition to the hydroxy group is from 1 to 5, with the proviso that when the phenolic ring contains 4 or 5 substituents the radicals —$(CH_2NR^2R^3)_n$ are in ortho or para positions.

2. The process of claim 1 wherein in addition to the dialkylaminomethylphenol another phenolic compound selected from the group consisting of hindered monohydric phenolic antioxidants and hindered bisphenolic antioxidants is also added to the stereoregular polymer prior to exposure of the polymer to substantial oxidative degradation conditions.

3. The process according to claim 2 wherein $R^2$ and $R^3$ are selected from the group consisting of methyl radicals and hydroxy alkyl radicals having two carbon atoms or are joined to constitute with the attached nitrogen atom a piperidino or morpholino ring, wherein R and R¹ are selected from the group consisting of hydrogen and alkyl radicals having 1 to 4 carbon atoms, wherein $n$ is an integer from 2 to 3, wherein the dialkylaminomethyl groups occupy at least one position ortho to the hydroxyl group and the total number of substituents on the phenolic ring is 3.

4. The process according to claim 3 where dialkylaminomethyl groups occupy both ortho positions.

5. The process according to claim 2 wherein the dialkylaminomethyl phenol is selected from the group consisting of 2,4,6-tris(dimethylaminomethyl) phenol and 2,6-bis(dimethylaminomethyl)-4-tert.butylphenol.

6. The process according to claim 2 wherein the stereoregular polymer is selected from the group consisting of cis-1,4-polybutadiene and high cis-1,4-polyisoprene.

7. The process according to claim 1 wherein R is hydrogen and $R^1$ is a tertiary nonyl radical.

8. The process according to claim 1 wherein the dialkylaminomethylphenol is 2,6-bis(dimethylaminomethyl)-4-tert.nonyl phenol.

9. The process according to claim 1 wherein R and $R^1$ are selected from the group consisting of hydrogen and alkyl radicals having 9 carbon atoms.

* * * * *